US00PP11175P

United States Patent [19]

Pouw

[11] Patent Number: Plant 11,175

[45] Date of Patent: Jan. 11, 2000

[54] HYBRID TEA ROSE PLANT NAMED 'RUILIRO'

[75] Inventor: Anton A. Pouw, PL DE Kwakel, Netherlands

[73] Assignee: De Ruiter's Nieuwe Rozen B.V., Pl De Kwakel, Netherlands

[21] Appl. No.: 09/028,631

[22] Filed: Feb. 24, 1998

[51] Int. Cl.[7] ..... A01H 5/00

[52] U.S. Cl. ..... Plt./137

[58] Field of Search ..... Plt./137, 138, 130, Plt./132

[56] References Cited

U.S. PATENT DOCUMENTS

P.P. 6,599 2/1989 Ohkawa ..... Plt./137
P.P. 7,895 6/1992 Marciel ..... Plt./137

*Primary Examiner*—Howard J. Locker
*Attorney, Agent, or Firm*—Christie, Parker & Hale, LLP

[57] ABSTRACT

A new variety of hybrid tea rose plant producing pink blend flowers.

2 Drawing Sheets

BACKGROUND OF THE INVENTION

The present invention relates to a new and distinct variety of rose plant of the hybrid tea rose class which was created by crossing undistributed, unnamed and unpatented seedlings as seed and pollen parents in The Netherlands. The varietal denomination of the new variety is 'Ruiliro'.

SUMMARY OF THE INVENTION

Among the novel characteristics possessed by this new variety which distinguish it from its parents and all other varieties of which I am aware are its attractive pink blend flowers.

Asexual reproduction by budding of the new variety as performed in The Netherlands, shows that the foregoing and other distinguishing characteristics come true to form and are established and transmitted through succeeding propagations. The new variety has been reproduced through propagation by cuttings, grafting, budding and micropropagation.

BRIEF DESCRIPTION OF ILLUSTRATIONS

The accompanying two photographic illustrations show the new variety of hybrid tea rose plant in color as true as it is reasonably possible to attain in color illustrations of this character.

The first illustration is a close up view of the bloom, peduncle, and foliage.

The second illustration shows a new shoot, 1; compound 3-leaflet leaf, 2; compound 5-leaflet leaf (partially cut-off), 3; compound 7-leaflet leaf, 4; stem, 5; buds, 6 and 7; a flower about ⅓ to ½ open, 8; a flower fully open, 9; and flowering stems 10, 11, and 12, with reproductive organs displayed.

DESCRIPTION OF THE NEW VARIETY

The following is a detailed description of the new variety, with color terminology in accordance with The Royal Horticultural Society Colour Chart (R.H.S.C.C.) and horticultural terminology in accordance with standard terminology used in UPOV-approved horticultural guidelines. The terminology used in color descriptions herein refers to plate numbers in the aforementioned color chart. Phenotypic expression may vary depending upon growing conditions under different climate, soil, and cultivation conditions.

Parentage: Seed and pollen parents are unnamed seedlings. Class: Hybrid Tea.

The following further horticultural description is based on observations made of specimens grown under glass in Quito, Ecuador.

FLOWER

Blooming habit: Nearly continuous.

A. Bud:

(1) *Size*.—About 5 cm long by about 2 to 4 cm wide, before sepals fall. About 5 to 6 cm long by about 4 cm wide, after sepals separate further.

(2) *Form*.—Ovate (shape of longitudinal section just before separation of sepals); urn-shaped after sepals part and petals begin to separate.

(3) *Color*.—Before sepals separate, white to near 56D with deeper tone, near 55C at petal edge becoming lighter until becoming near 4D at point of petal attachment.

(4) *Sepals*.—One to three are longer than bud, most very foliaceous; near 147A on top surface, lighter, near 147B, on undersurface.

(5) *Peduncle*.—Long: Strength-erect, strong. Color near 138A to 138B.

B. Flower: Medium; viewed from side — (a) upper part of fully opened flower, convex; (b) lower part of fully opened flower, concave.

(1) *Size*.—Average size when fully expanded — about 7 to 9 cm at about full open.

(2) *Borne*.—Singly, one to a stem.

(3) *Form*.—Mainly spiral imbricated, some outer petals have pointed apices, some inner petals ruffled and some roll under; somewhat recessed center in open bloom.

(4) *Petalage*.—Fully double, about 23.

(5) *Color*.—After sepals part and petals unfurl color of petal top surface near edges appears near 56C to 56D with washing of deeper tones, near 62C to 62D, especially on outer petals, washing on outer most petals is between 62D and 62C. Petal undersurface exhibits same coloration as top surface but with more matte appearance and outer edge of outer most petals may show greenish edges. Color at point of petal attachment is near 62D to 3D to 4D. Overall tonality from a distance is unusual pink blend with light pink center.

(6) *Peduncle*.—Generally smooth.

(7) *Fragrance*.—Absent or weak.

(8) *Length of stems*.—About 60 cm to 100 cm.

Petals:

(1) *Texture*.—Crisp.

(2) *Appearance*.—Inside velvety and outside satiny.

(3) *Form and size*.—Broad, medium, medium undulation of margin.

(4) *Arrangement*.—Regularly arranged, imbricated.

(5) *Petaloids*.—Several, about 2 to 5.

(6) *Lasting quality*.—Long-lasting quality on plant (about 20 days) and after cutting (about 14 days).

REPRODUCTIVE ORGANS

A. Stamens, filaments and anthers:

*Arrangement and color*.—Regularly arranged around styles; color of filaments — white to pale yellow.

B. Pollen: Color — near 19B to 19C.

C. Styles: Long, stigma above mouth of receptacle, white.

D. Stigmas: Yellow.

E. Hip: Pitcher-shaped; small seed vessel at petal fall.

PLANT

A. Form: Narrow, bushy, average disease resistance; height about 1.5 m, spread about 0.5 m.

B. Growth: Vigorous.

C. Foliage: Compound 3, 5 and 7 leaflets (1) *Size*.—3-leaflet leaf, terminal leaflet about 7 cm long; 5-leaflet leaf, terminal leaflet about 5 to 6 cm long; 7-leaflet leaf, terminal leaflet about 5 to 6 cm long.

(2) *Quantity*.—Abundant.

(3) *Color*.—Juvenile foliage — top near 187A underside grey brown near 187B; absent or weak anthocyanin coloration, (shoot about 20 cm long); mature top leaf color — near 137A; undersurface near 138B.

(4) *Shape*.—Broad oval.

(5) *Texture*.—Upper side is medium glossy; underside is matte.

(6) *Edge*.—Serrate.

(7) *Serration*.—Serrulate, obtuse apices.

(8) *Leaf stem*.—Color — near 138B.

(9) *Stipules*.—About 1.8 cm, green color same as leaves.

(10) *Leaflets*.—Cross section — flat; weak undulation of margin; terminal leaflet — medium length and medium width; rounded base.

D. Wood:

(1) *New wood*.—Color — young shoots have medium anthocyanin; coloration — bronze to reddish brown, near 187B.

(2) *Old wood*.—Color — green, near 137C.

E. Prickles (thorns):

(1) *Prickles*.—Present; quantity few on lower part, top ⅓ no prickles; shape of lower side — concave, near 138C, on new shoots about 4 prickles between internodes, near 187C; short prickles absent or very few, long prickles few. Position — irregular when they appear.

What is claimed is:

1. A new and distinct hybrid tea rose plant of the variety substantially as shown and described.

* * * * *

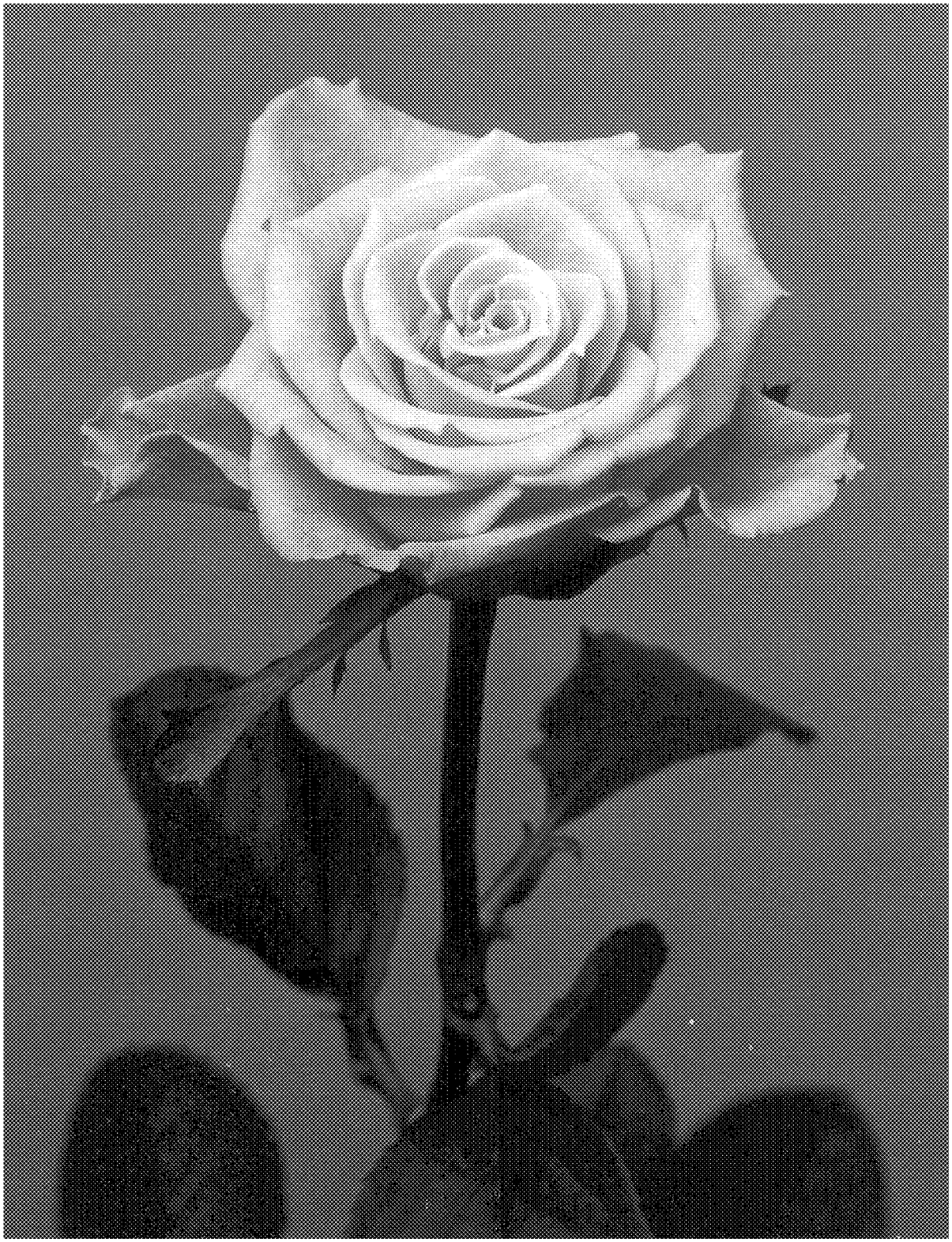

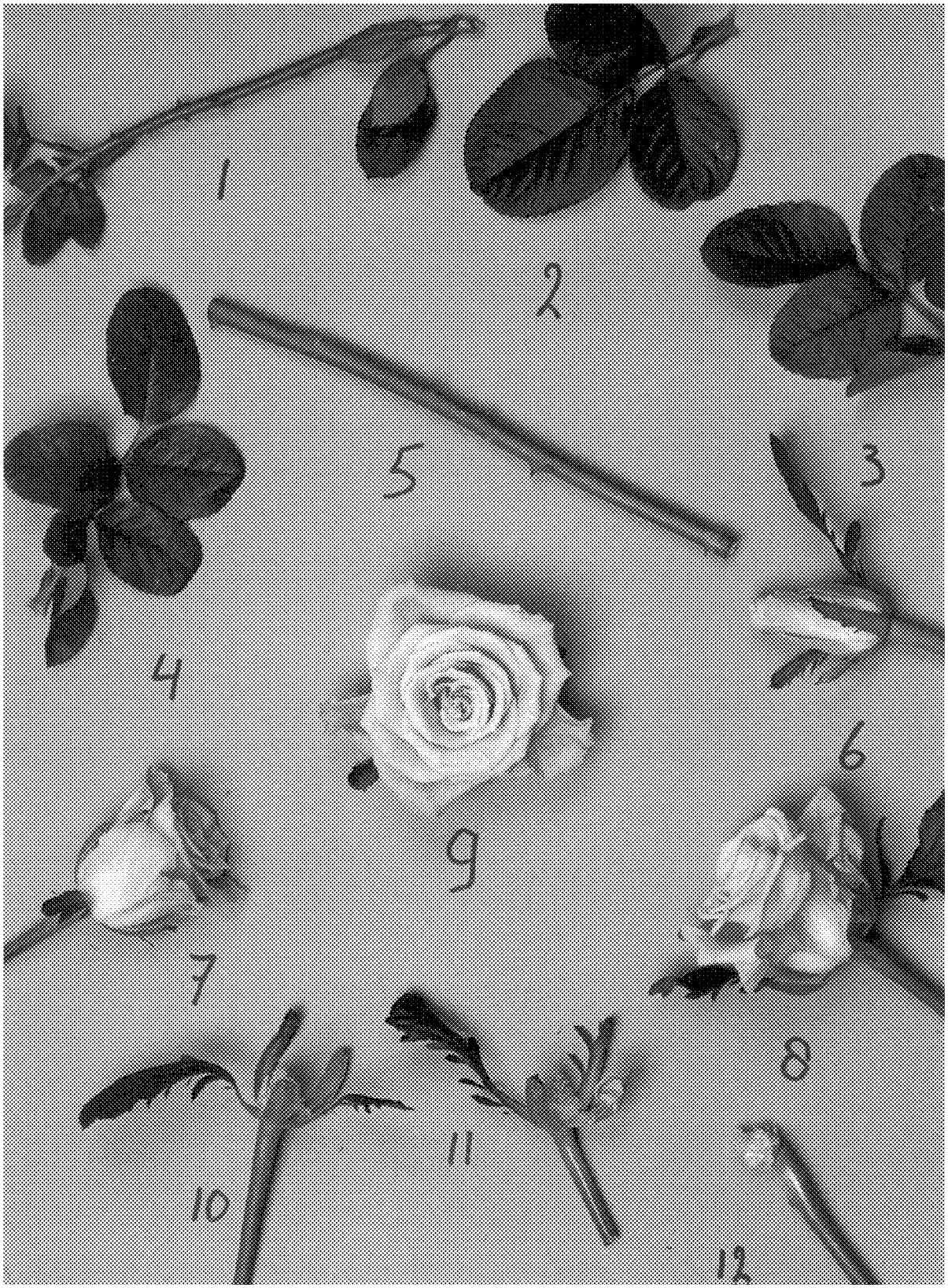
1
2
3
4
5
6
7
8
9
10
11
12